United States Patent [19]  [11] 4,283,508
Maender  [45] Aug. 11, 1981

[54] FRAGRANT PREVULCANIZATION INHIBITORS

[75] Inventor: Otto W. Maender, Copley, Ohio

[73] Assignee: Monsanto Company, St. Louis, Mo.

[21] Appl. No.: 152,279

[22] Filed: May 22, 1980

[51] Int. Cl.$^3$ .............................................. C08F 8/34
[52] U.S. Cl. ...................................... 525/351; 260/5;
  260/45.85 A; 260/45.85 N; 260/45.9 NC;
  260/780; 260/781; 260/782
[58] Field of Search ............ 525/351; 260/5, 45.85 A,
  260/45.9 NC, 780, 45.85 N, 781, 782

[56] References Cited

U.S. PATENT DOCUMENTS

| | | |
|---|---|---|
| 3,473,667 | 10/1969 | Coran et al. .......................... 260/780 |
| 3,546,185 | 12/1970 | Coran et al. .......................... 260/780 |
| 3,705,135 | 12/1972 | Wolfinger ............................. 260/780 |
| 3,780,001 | 12/1973 | Son ....................................... 525/351 |
| 3,855,262 | 12/1974 | Coran ................................. 260/453 R |
| 3,895,060 | 7/1975 | Son ....................................... 525/351 |
| 3,910,864 | 10/1975 | Son ....................................... 260/780 |
| 3,965,077 | 6/1976 | Son ....................................... 525/351 |
| 4,006,140 | 2/1977 | Son ...................................... 260/246 B |
| 4,156,680 | 5/1979 | Morita ................................... 260/780 |
| 4,165,310 | 8/1979 | Morita ............................. 260/45.85 A |

Primary Examiner—William F. Hamrock
Attorney, Agent, or Firm—Larry R. Swaney

[57] ABSTRACT

Alkyl thiosalicylate prevulcanization inhibitors having a pleasant odor are described.

13 Claims, No Drawings

FRAGRANT PREVULCANIZATION INHIBITORS

This application relates to improved inhibitors of premature vulcanization, to improved vulcanizable rubber compositions, and, more particularly, to sulfenamide-type inhibitors containing carboalkoxyphenyl moieties.

BACKGROUND OF THE INVENTION

Prevulcanization inhibitors having a characteristic nucleus of

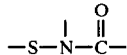

are well known and widely used in the rubber industry. Some workers object to a malodorous quality associated with inhibitor use. The objectionable odor is not necessarily associated with the inhibitor alone, but seems to develop as a consequence of contact with the skin or mucous membrane. Moreover, the bad odor is not always apparent immediately upon exposure, but generally develops several minutes after exposure. Since the unpleasant odor or taste is not immediately obvious, it is sometimes called "after-odor," i.e., an odor which arises "after" use of the inhibitor.

SUMMARY OF THE INVENTION

A class of prevulcanization inhibitors has been discovered which exhibit a characteristic fragrance, i.e., they have a sweet, pleasant "after odor." The improved odor is believed to be due to the presence of an alkyl thiosalicylate moiety in the inhibitor molecule. The other part of the molecule is an amide inhibitor moiety. The improved inhibitors of the invention are characterized by the formula

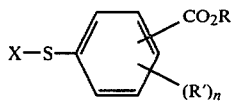

in which X is an amide inhibitor moiety, R is alkyl of 1–8 carbon atoms, R' is alkyl of 1–8 carbon atoms, alkoxy of 1–8 carbon atoms, —CO$_2$R, or halo, and n is 0, 1 or 2. The —CO$_2$R and R' radicals may be attached to any of the available carbon atoms of the benzene ring. However, compounds in which the carboalkoxy radical is in the 2-position and n is 0 are preferred.

The radical represented by X can be any amide moiety known to exhibit inhibitor activity when an organic radical is attached through a sulfur to a nitrogen atom of the amide moiety. Suitable compounds include those which contain more than one of the alkyl thiosalicylate moieties, i.e., compounds in which two thiosalicylate moieties are attached to the same amide nitrogen atom and compounds in which two or more thiosalicylate moieties are attached to different amide nitrogen atoms. The term "amide inhibitor moiety" means a compound having a characteristic nucleus of

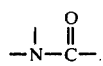

In the compounds of the invention, at least one of the unsatisfied valences of the nitrogen is satisfied by a thiosalicylate moiety. Examples of satisfactory amide inhibitor moieties are described in the following U.S. patents, the disclosures of which are incorporated herein by reference: U.S. Pat. No. 3,427,319; U.S. Pat. No. 3,473,667; U.S. Pat. No. 3,546,185; U.S. Pat. No. 3,780,001; U.S. Pat. No. 3,855,262; and U.S. Pat. No. 4,156,680.

Examples of suitable amide moieties are radicals derived by removing a hydrogen atom from one or more atoms of nitrogen in 2-benzimidazolinone, 2-imidazolidinone, 2-benzothiazolone, 2-thiazolone, phthalimide, succinimide, glutarimide, hexahydrophthalimide, maleimide, hydantoin, urea, naphthalimide, oxamide, oxanilide, phenylcarbamic acid ester, formamide, formanilide, acetamide, benzamide, acetanilide, benzanilide, propionamide, butyramide, pivalamide, valeramide, and hexanamide.

Illustrative examples of inhibitors of the invention are:
N-(2-carbomethoxyphenylthio)phthalimide
N-(2-carbomethoxyphenylthio)succinimide
N-(2-carbomethoxyphenylthio)glutarimide
N-(2-carbomethoxyphenylthio)hexahydrophthalimide
N-(2-carbomethoxyphenylthio)naphthalimide
N-(2-carbomethoxyphenylthio)maleimide
N-(2-carbomethoxyphenylthio)formamide
N-(2-carbomethoxyphenylthio)formanilide
N-(2-carbomethoxyphenylthio)acetamide
N-(2-carbomethoxyphenylthio)acetanilide
N-(2-carbomethoxyphenylthio)benzamide
N-(2-carbomethoxyphenylthio)benzanilide
N-(2-carbomethoxyphenylthio)propionamide
N-(2-carbomethoxyphenylthio)butyramide
N-(2-carbomethoxyphenylthio)valeramide
N-(2-carbomethoxyphenylthio)hexanamide
N-(2-carbomethoxyphenylthio)hydantoin
N-(2-carbomethoxyphenylthio)urea
N-(2-carbomethoxyphenylthio)2-benzimidazoline
N-(2-carbomethoxyphenylthio)2-imidazolidinone
N-(2-carbomethoxyphenylthio)2-benzothiazolone
N-(2-carbomethoxyphenylthio)2-thiazolone
N-(2-carbomethoxyphenylthio)oxamide
N-(2-carbomethoxyphenylthio)oxanilide
N-(2-carbomethoxyphenylthio)phenylcarbamic acid ethyl ester
N-(2-carbomethoxyphenylthio)phenylcarbamic acid benzyl ester
N-(2-carbomethoxyphenylthio)phenylcarbamic acid phenyl ester
N-(2-carbomethoxyphenylthio)phenylcarbamic acid cyclohexyl ester
N,N-di(2-carbomethoxyphenylthio)urea
N,N'-bis(2-carbomethoxyphenylthio)urea
N,N'-bis(2-carbomethoxyphenylthio)oxamide
N,N'-bis(2-carbomethoxyphenylthio)oxanilide
N,N-bis(2-carbomethoxyphenylthio)acetamide
N,N-bis(2-carbomethoxyphenylthio)benzamide
N,N'-bis(2-carbomethoxyphenylthio)hydantoin
N,N'-bis(2-carbomethoxyphenylthio)2-benzimidazolinone
N,N'-bis(2-carbomethoxyphenylthio)2-imidazolidinone
N-(2,4-dicarbomethoxyphenylthio)phthalimide
N-(2-carbethoxyphenylthio)phthalimide
N-(2-carbopropoxyphenylthio)phthalimide
N-(2-carbobutoxyphenylthio)phthalimide
N-(2-carbomethoxy-4-methylphenylthio)phthalimide
N-(2-carbomethoxy-5-chlorophenylthio)phthalimide N-(2-carbomethoxy-4-methoxyphenylthio)phthalimide
N-(2-carbomethoxy-4,6-dichlorophenylthio)phthalimide
and corresponding carboalkoxyphenylthio and carboalkoxy-substituted phenylthio derivatives of the above named amides and imides.

The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions containing a sulfur vulcanizing agent such as an amine disulfide or a polymeric polysulfide but preferably, the vulcanizing agent is elemental sulfur (usually about 0.5–5 parts by weight of sulfur are used per 100 parts by weight of rubber). Rubber compositions containing organic accelerating agents are particularly improved by the inhibitors of the invention, with compositions containing 2-mercaptobenzothiazole or benzothiazole sulfenamide accelerators being preferred. Any organic accelerating agent in an amount effective (generally about 0.1–5 parts by weight accelerator per 100 parts by weight rubber) to accelerate the sulfur vulcanization of rubber is satisfactory in the practice of this invention. The inhibitors of the invention are effective with any sulfur-vulcanizable natural and synthetic rubber and mixtures thereof. Diene rubbers are preferred. Suitable accelerators and rubbers are described in U.S. Pat. No. 3,546,185, Col. 9, lines 53–75; Col. 10, lines 15–21; and U.S. Pat. No. 3,780,001, Col. 4, lines 43–72; Col. 5, lines 5–33, respectively, the disclosures of which are incorporated herein by reference. The vulcanizable composition may also contain conventional compounding ingredients such as reinforcing pigments, extenders, processing oils, antidegradants and the like.

Small amounts of inhibitors are effective to inhibit premature vulcanization. Inprovements in processing safety may be observed with 0.05 parts or less of inhibitor per 100 parts of rubber. Although there is no upper limit in the amount of inhibitor used, generally the amount does not exceed 5 parts inhibitor per 100 parts of rubber. Typically, the amount of inhibitor added is about 0.1 to 2.5 parts per 100 parts of rubber with amounts of about 0.2 to 1 part inhibitor per 100 parts of rubber being preferred. Methods for determining scorch times and curing characteristics of rubber stocks used in illustrating this invention are described in U.S. Pat. No. 3,546,185, Col. 13, lines 30–53. Stress-strain properties are reported in megapascals (MPa).

PREFERRED EMBODIMENTS

A suitable procedure for preparing inhibitors of the invention comprises adding at about 0°–75° C., usually at room temperature, a sulfenyl chloride to a slurry or solution of an amide or imide in an inert organic medium, such as toluene or methylene dichloride, in the presence of an acid acceptor such as triethylamine. The sulfenyl chloride may be prepared by chlorination of an appropriate disulfide, for example, by chlorination of a slurry of 2,2'-carbomethoxyphenyl disulfide in toluene. After the sulfenyl chloride is reacted, the amine salt by-product is removed by filtration. The filtrate is washed with water and dried over sodium sulfate. The product is recovered by evaporating the solvent and is further purified by conventional procedures.

An alternate procedure for preparing inhibitors of the invention comprises reacting a sulfenyl chloride with an alkali metal (preferably sodium or potassium) salt of an amide or imide. The alkali metal salt intermediate may be prepared by reacting an alkali metal alcoholate and amide or imide in an inert organic medium and removing the alcohol by-product by distillation. The resulting slurry of amide (imide) alkali metal salt may be reacted, without further purification, with the sulfenyl chloride reactant. The sulfenyl chloride is generally added dropwise at room temperature to the aforesaid slurry. Salt by-product and any unreacted alkali metal salt intermediate is recovered by filtration. When the product is insoluble, the filter cake is washed with water to remove salt by-product. When the product is soluble in the reaction medium, the product is recovered by evaporation. Generally, the product is further purified by recrystallization from an appropriate solvent, such as, toluene or mixture of hexane and methylene dichloride. Product identification is confirmed by liquid chromatographic analysis and nuclear magnetic spectral analysis.

The following compounds are prepared as described above by reacting 2-carbomethoxybenzene sulfenyl chloride with the appropriate amide intermediate. N-(2-carbomethoxyphenylthio)phthalimide, m.p. 257°–260° C.; N-(2-carbomethoxyphenylthio)-2-benzothiazolone, m.p. 166.5°–168° C.; bis-N,N-(2-carbomethoxyphenylthio)formamide, m.p. 222°–223° C.; (2-carbomethoxyphenylthio)phenylcarbamic acid, methyl ester, m.p. 125.5°–126° C.; N-(2-carbomethoxyphenylthio)formanilide, m.p. 105°–106° C.; N-(2-carbomethoxyphenylthio)succinimide, m.p. 199°–200° C.; bis-N,N-(2-carbomethoxyphenylthio)acetamide, m.p. 200°–201.5° C.; N-(2-carbobutoxyphenylthio)succinimide, m.p. 158° C.

The above compounds, in essentially pure form, are either odorless or exhibit a pleasing, fruity fragrance. To further assess the odor characteristics of sulfenamide inhibitors, an accelerated odor test was developed which is believed to simulate conditions which may exist in the mucous membrane. The test is based upon glutathione, a material present in the skin and mucous membrane which reacts with sulfenamides. The test consists of charging at room temperature, 20 milligrams of a test compound to a closed glass container containing 20 milligrams of glutathione in 5 milliliters of water. The samples are allowed to stand overnight and then human subjects rate the odor of the samples on a scale of pleasant to objectionable. A glutathione control is rated as being essentially odorless. Samples of N-(2-carbomethoxyphenylthio) amides of the invention are rated as being odorless or having a pleasant fragrance. The odor of N-(carbobutoxyphenylthio)succinimide is rated as inferior (slightly more objectionable) than N-(carbomethoxyphenylthio)succinimide. Samples of prior art sulfenamide inhibitors, for example, N-(phenylthio)succinimide and N-(phenylthio)phthalimide, are rated as having a moderate to objectionable odor.

A natural rubber masterbatch is prepared by conventional mixing procedures. Portions of the masterbatch containing no inhibitor are controls. A quantity of inhibitor is incorporated into other portions of the masterbatch. Accelerator and sulfur are also incorporated to form vulcanizable compositions. The properties of the vulcanizable compositions and vulcanizates are measured by conventional methods as described above. The Mooney scorch is determined at 135° C. Vulcanizates are prepared by curing at 153° C. for the time required to obtain optimum cure as indicated by Rheometer data. Santocure® NS accelerator is N-(t-butyl)-2-benzothiazole sulfenamide. Thiofide ® accelerator is benzothiazolyl disulfide. DPG is diphenylguanidine, a cure activator. The composition of the masterbatch of Table 3 is the same except 2.5 parts of sulfur are also included. The results are shown in the tables.

| Natural Rubber Masterbatch (Parts by Weight) | |
|---|---|
| Smoked Sheets | 100 |
| Carbon Black | 40 |
| Processing Oil | 10 |
| Zinc Oxide | 5 |
| Stearic Acid | 1 |
| Wax | 2 |
| | 158 |

TABLE 1

| | 1 | 2 | 3 | 4 |
|---|---|---|---|---|
| Masterbatch | 158 | 158 | 158 | 158 |
| Sulfur | 2.5 | 2.5 | 2.5 | 2.5 |
| Santocure ® NS Accelerator | 0.6 | 0.6 | 0.6 | 0.6 |
| N-(2-carbomethoxyphenylthio)-phthalimide | — | 0.48 | — | — |
| N-(2-carbomethoxyphenylthio)-2-benzothiazolone | — | — | — | 0.4 |
| Mooney Scorch @ 135° C. | | | | |
| $t_5$, minutes | 12.5 | 17.2 | 16.1 | 27.5 |
| % increase in scorch safety | — | 38 | — | 71 |
| Stress-Strain @ 153° C. | | | | |
| UTS, MPa | 27.1 | 24.3 | 24.7 | 26.2 |
| $M_{300}$, MPa | 7.1 | 6.8 | 6.7 | 6.7 |
| Elong., % | 670 | 650 | 640 | 690 |

TABLE 2

| | 1 | 2 | 3 | 4 | 5 |
|---|---|---|---|---|---|
| Masterbatch | 158 | 158 | 158 | 158 | 158 |
| Sulfur | 2.5 | 2.5 | 2.5 | 2.5 | 2.5 |
| Santocure ® NS Accelerator | 0.6 | 0.6 | 0.6 | 0.6 | 0.6 |
| N-(2-carbomethoxyphenylthio)-2-benzothiazolone | — | 0.4 | — | — | — |
| bis-N,N-(2-carbomethoxyphenylthio)formamide | — | — | 0.4 | — | — |
| (2-carbomethoxyphenylthio)-phenyl-carbamic acid, methyl ester | — | — | — | 0.4 | — |
| (2-carbomethoxyphenylthio)-formanilide | — | — | — | — | 0.4 |
| Mooney Scorch @ 135° C. | | | | | |
| $t_5$, minutes | 15.9 | 27.1 | 24.6 | 18.2 | 25.7 |
| % increase in scorch safety | — | 70 | 55 | 21 | 62 |
| Stress-Strain @ 153° C. | | | | | |
| UTS, MPa | 24.0 | 24.6 | 21.5 | 23.4 | 25.0 |
| $M_{300}$, MPa | 7.6 | 7.5 | 7.2 | 7.5 | 7.5 |
| Elong., % | 610 | 620 | 580 | 610 | 620 |

TABLE 3

| | 1 | 2 | 3 | 4 | 5 |
|---|---|---|---|---|---|
| Masterbatch | 160.5 | 160.5 | 160.5 | 160.5 | 160.5 |
| 2-mercaptobenzothiazole | 0.6 | 0.6 | 0.6 | 0.6 | 0.6 |
| N-(2-carbomethoxyphenylthio)-2-benzothiazolone | — | 1.14 | — | — | — |
| bis-N,N-(2-carbomethoxyphenylthio) formamide | — | — | 0.68 | — | — |
| (2-carbomethoxyphenylthio)-phenylcarbamic acid, methyl ester | — | — | — | 1.14 | — |
| (2-carbomethoxyphenylthio)-formanilide | — | — | — | — | 1.03 |
| Mooney Scorch @ 135° C. | | | | | |
| $t_5$, minutes | 8.1 | 24.9 | 13.9 | 19.1 | 23.3 |
| % increase in scorch safety | — | 207 | 72 | 136 | 188 |
| Stress-Strain @ 153° C. | | | | | |
| UTS, MPa | 11.0 | 16.2 | 15.4 | 15.3 | 16.1 |
| $M_{300}$, MPa | 3.9 | 5.0 | 5.1 | 4.6 | 5.0 |
| Elong., % | 540 | 600 | 570 | 590 | 580 |

TABLE 4

| | 1 | 2 | 3 | 4 | 5 | 6 |
|---|---|---|---|---|---|---|
| Masterbatch | 158 | 158 | 158 | 158 | 158 | 158 |
| Sulfur | 2.5 | 2.5 | 2.5 | 2.5 | 2.5 | 2.5 |
| Santocure ® NS | 0.6 | 0.6 | 0.6 | — | — | — |
| Thiofide ® | — | — | — | 0.8 | 0.8 | 0.8 |
| DPG | — | — | — | 0.2 | 0.2 | 0.2 |
| N-(2-carbomethoxyphenylthio)succinimide | — | 0.4 | — | — | 0.5 | — |
| bis-N,N'-(2-carbomethoxyphenylthio)acetamide | — | — | 0.4 | — | — | 0.5 |
| Mooney Scorch @ 135° C. | | | | | | |
| $t_5$, minutes | 13.8 | 22.1 | 17.3 | 6.1 | 8.2 | 6.9 |
| % increase in scorch safety | — | 60 | 25 | — | 34 | 13 |
| Stress-Strain @ 153° C. | | | | | | |
| UTS, MPa | 24.9 | 23.5 | 24.1 | 25.4 | 24.1 | 22.0 |
| $M_{300}$, MPa | 10.2 | 9.3 | 9.8 | 9.0 | 8.6 | 8.0 |
| Elong., % | 540 | 520 | 520 | 560 | 560 | 540 |

The data show that all of the compounds are effective inhibitors and increase scorch safety of vulcanizable compositions containing either 2-mercaptobenzothiazole or sulfenamide-type accelerator. Similar results are obtained with compositions containing styrene-butadiene rubber.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A vulcanizable composition comprising sulfur-vulcanizable rubber, sulfur-vulcanizing agent, organic accelerating agent and, in an amount effect to inhibit premature vulcanization, a compound of the formula:

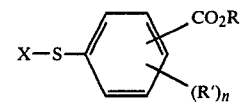

in which X is an amide inhibitor moiety, R is alkyl of 1-8 carbon atoms, R' is alkyl of 1-8 carbon atoms, alkoxy of 1-8 carbon atoms, —CO$_2$—R, or halo, and n is 0, 1 or 2.

2. The composition of claim 1 in which —CO$_2$R is in the 2-position.

3. The composition of claim 2 in which the amide moiety is a radical derived from the group consisting of 2-benzimidazolinone, 2-imidazolidinone, 2-benzothiazolone, 2-thiazolone, phthalimide, succinimide, glutarimide, hexahydrophthalimide, maleimide, hydantoin, urea, naphthalimide, oxamide, oxanilide, phenylcarbamic acid ester, formamide, formanilide, acetamide, benzamide, acetanilide, benzanilide, propionamide, butyramide, pivalamide, valeramide, and hexanamide.

4. The composition of claim 3 in which the vulcanizing agent is elemental sulfur and the rubber is a diene rubber.

5. The composition of claim 4 in which the accelerating agent is 2-mercaptobenzothiazole or a benzothiazole sulfenamide.

6. The composition of claim 5 in which n is O and R is alkyl of 1–4 carbon atoms.

7. The composition of claim 6 in which X is a radical derived from the group consisting of phthalimide, succinimide, 2-benzothiazolone, oxamide, oxanilide, formamide, formanilide, or phenylcarbamic acid ester.

8. The composition of claim 7 in which R is methyl.

9. The composition of claim 8 in which X is 2-benzothiazolon-1-yl.

10. The composition of claim 8 in which X is

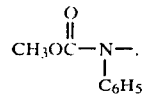

11. The composition of claim 8 in which X is

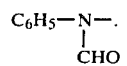

12. The composition of claim 8 in which X is N-succinimidyl.

13. The composition of claim 8 is which X is N-phthalimidyl.

* * * * *